United States Patent [19]
Mirhashemi et al.

[11] Patent Number: 6,142,996
[45] Date of Patent: Nov. 7, 2000

[54] METHODS USEABLE FOR FORMING SMALL OPENINGS IN THE LENS CAPSULES OF MAMMALIAN EYES

[75] Inventors: Soheila Mirhashemi; Michael Mittelstein, both of Laguna Niguel; John T. Sorensen, Costa Mesa, all of Calif.

[73] Assignee: Optex Ophthalmologics, Inc., San Juan Capistrano, Calif.

[21] Appl. No.: 09/350,829

[22] Filed: Jul. 9, 1999

Related U.S. Application Data

[62] Division of application No. 08/744,404, Nov. 7, 1996, Pat. No. 5,957,921.

[51] Int. Cl.⁷ .................................................. A61B 17/36
[52] U.S. Cl. .............................. 606/41; 606/107; 606/45; 606/180; 604/22
[58] Field of Search ........................... 606/4–6, 107, 606/35, 41, 45, 46, 48, 50, 171, 179, 180; 604/22

[56] References Cited

U.S. PATENT DOCUMENTS

| | | |
|---|---|---|
| 4,481,948 | 11/1984 | Sole .......................................... 606/45 |
| 4,674,499 | 6/1987 | Pao ............................................ 606/50 |
| 5,413,574 | 5/1995 | Fugo . |
| 5,533,999 | 7/1996 | Hood et al. .................................. 606/5 |
| 5,722,945 | 3/1998 | Anis et al. ................................. 604/22 |
| 5,749,871 | 5/1998 | Hood et al. ............................... 606/50 |
| 5,925,045 | 7/1999 | Reimels et al. ........................... 606/48 |

*Primary Examiner*—Linda C. M. Dvorak
*Assistant Examiner*—David M. Ruddy
*Attorney, Agent, or Firm*—Robert D. Buyan; Stout, Uxa, Buyan & Mullins, LLP

[57] ABSTRACT

A device and system for creating small (e.g., less than 3 mm and preferably about 1 mm in cross dimension) openings in the anterior lens capsule of a mammalian eye to facilitate insertion of lens reduction/removal device(s) and/or cannulae for injecting flowable lens replacement materials into the lens capsule. The device generally comprises a handpiece having an electrosurgical probe extending forwardly therefrom. The electrosurgical probe incorporates an annular tip electrode which is positionable in contact with the lens capsule, to create the desired less than 3 mm opening therein. The annular electrode tip may be either monopolar or bipolar in design.

9 Claims, 4 Drawing Sheets

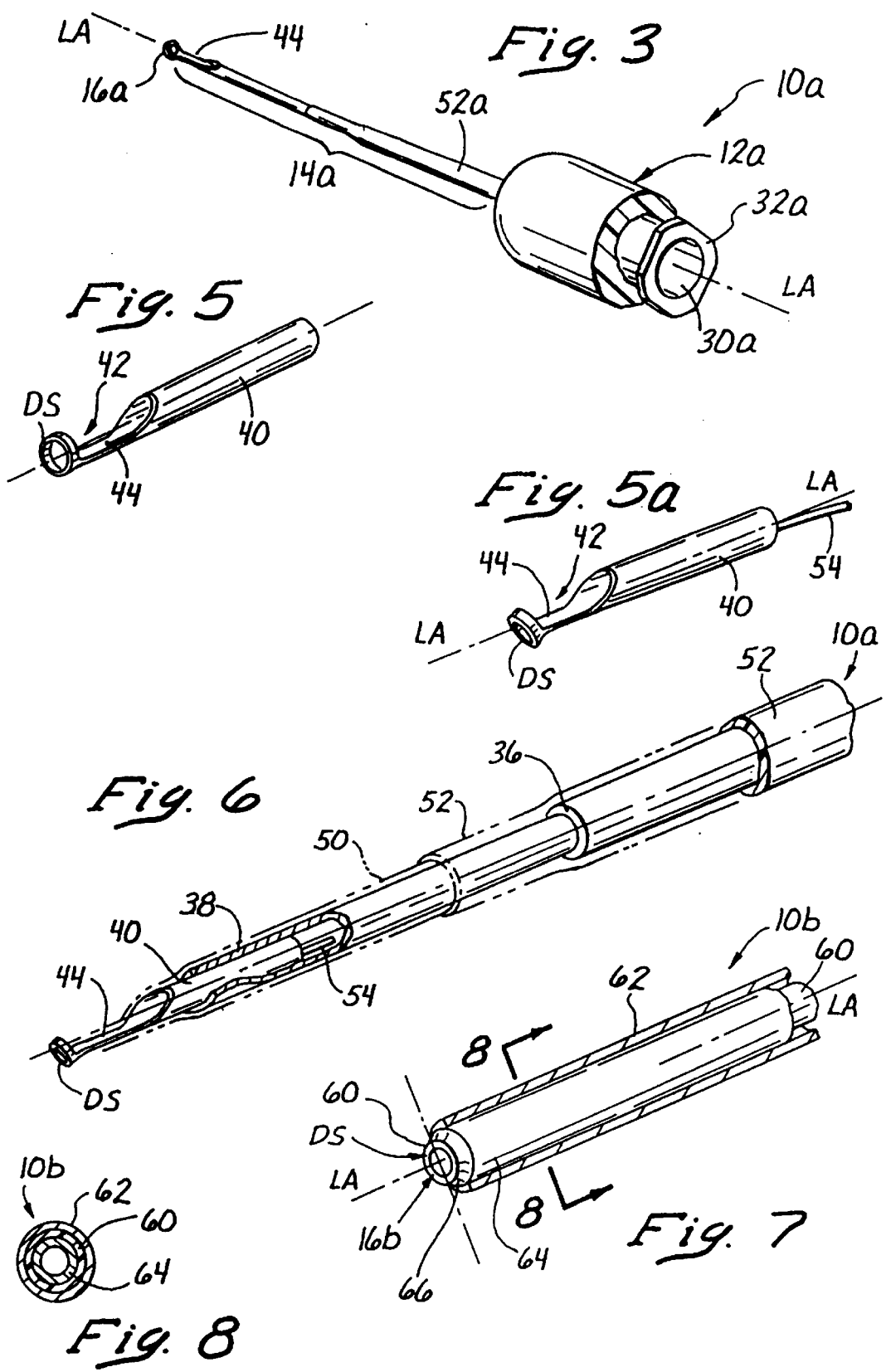

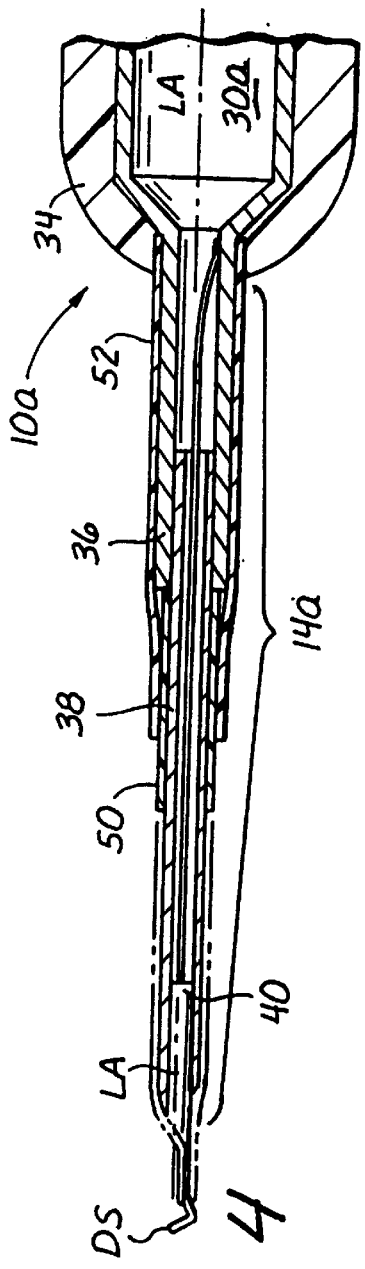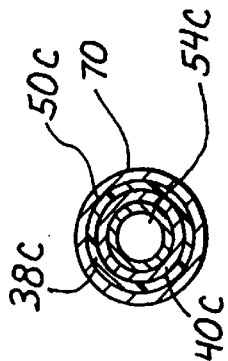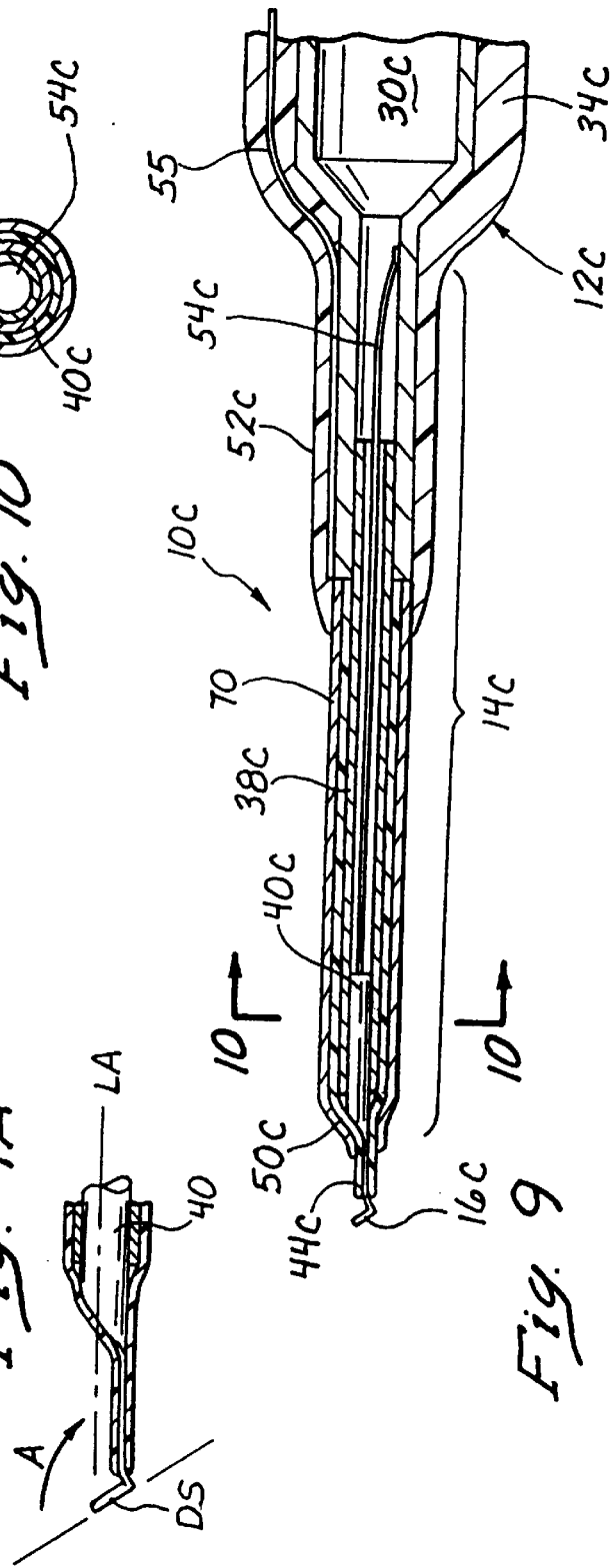

METHODS USEABLE FOR FORMING SMALL OPENINGS IN THE LENS CAPSULES OF MAMMALIAN EYES

This is a division of U.S. patent application Ser. No. 08/744,404 which was filed on Nov. 7, 1996 now U.S. Pat. No. 5,957,921.

FIELD OF THE INVENTION

The present invention relates generally to medical devices, and more particularly to an electrical surgical device which is usable to form relatively small (e.g., 1–2 mm) openings in the lens capsule of the eye.

BACKGROUND OF THE INVENTION

Cataracts have become one of the most common causes of visual impairment and blindness in our ageing population. Surgery is currently the only method of restoring vision to patients who have become visually impaired or blinded by cataracts.

Traditional cataract removal surgery requires the intact cataract-affected lens to be removed through a 7–10 mm incision formed in the anterior aspect of the lens capsule of the eye. After the in-tact cataract affected lens has been removed through the 7–10 mm incision, a prosthetic lens (e.g., a transparent lens formed of a biocompatable polymer) is then inserted through such 7–10 mm incision and implanted within the lens capsule to serve as a replacement for the previously-removed cataract-affected lens. These classic cataract removal procedures have proven to be successful in restoring vision, but often are associated with post-operative complications due to the large 7–10 mm incision formed in the lens capsule.

More recently, another surgical procedure, known as phacoemulsification, has been developed for removing cataract-affect lenses. In these phacoemulsification procedures, an ultrasonically vibrating probe is inserted into the lens capsule through an incision formed therein. The ultrasonically vibrating emulsification probe is then manipulated about to effect complete emulsification of the cataract-affected lens. The emulsified lens matter is then aspirated out of the lens capsule. Thereafter, the desired prosthetic lens replacement is inserted into the lens capsule. Although the diameter of the phacoemulsification probe may be relatively small, it is still typically necessary to utilize a capsular incision of 2.5–6.0 mm in length to allow the probe to be manipulated about sufficiently to accomplish complete emulsification and removal of the lens matter. Furthermore, it is often necessary to further enlarge the capsular incision through which the phacoemulsification probe was inserted to the usual 7–10 mm size to permit subsequent insertion of a preformed prosthetic lens implant into the lens capsule.

The need to form a relatively large incision in the anterior lens capsule to permit passage of a prosthetic lens replacement into the lens capsule may soon be obviated due to certain developments in the lens removal/replacement technology. For example, certain injectable lens replacement materials, known in the art and/or presently being developed, may be passed into the interior of the lens capsule through a needle or tubular cannula. Because these injectable lens replacement materials may be passed into the lens capsule through a relatively small opening, the advent of these injectable lens replacement materials may eliminate any need for the formation of large incisions in the lens capsule to allow a prosthetic lens to be inserted into the lens capsule.

Also, certain rotatable lens removing devices, such as those described in U.S. Pat. No. 5,437,678 (Sorensen) as well as in U.S. patent applications Ser. Nos. 08/421,421, and 08/658,846 may be inserted into the lens capsule through small (e.g., less than 3 mm) openings and may be held substantially stationary during lens reduction and removal, thereby avoiding any need for forming any large (e.g., greater than 3 mm) capsular incision.

In view of the development of modern injectable lens replacement materials and rotatable lens removing devices which may be inserted and operated through relatively small openings in the lens capsule, it is now possible to perform an entire cataract removal and prosthetic lens replacement, through a small (e.g., less than 3 mm) opening in the anterior lens capsule, while allowing the remainder of the anterior lens capsule to remain in-tact and unincised. However, the process of creating a small (e.g., less than 3 mm) opening in the anterior lens capsule is problematic due to the tendency of the lens capsule material to tear or "run" when punctured.

Accordingly, there presently exists a need for a new device capable of consistently making small (e.g., less than 3 mm) openings in the anterior lens capsule of the eye.

SUMMARY OF THE INVENTION

The present invention provides electrosurgical devices and methods for forming small (e.g., less than 3 mm) openings in the anterior lens capsule of the mammalian eye.

In accordance with the invention, there is provided an electrosurgical probe device generally comprising: a) an elongate probe which has a proximal end, a distal end and a longitudinal axis projectable therethrough, and, b) an annular electrode tip located on the distal end of said elongate probe, said annular electrode tip having a lens capsule contacting surface which lies substantially in, or is substantially disposable in, a plane that is nonparallel to the longitudinal axis of the probe, said probe being thereby insertable into the eye such that the lens capsule contacting surface of the annular electrode tip is in contact with the lens capsule, whereby passage of electrical current through annular electrode tip will create an opening in the lens capsule.

Further in accordance with the invention, the above-summarized probe device may be of a monopolar or bipolar type. If the device is of a monopolar type, a second electrode (e.g., a plate electrode) will necessarily be attached to, or placed in sufficient proximity to be electrically coupled to, the body of the patient to complete an electrical circuit or between the electrode tip of the device and the second electrode. On the other hand, if the device is of the bipolar type, the second electrode will be formed or mounted upon the body of the probe, and no externally-attached second electrode will be required.

Still further in accordance with the invention, there is provided an electrosurgical system for forming small (e.g., less than 3 mm) openings in the anterior lens capsule of the mammalian eye, said system comprising an electrosurgical probe device of the above-described character, further in combination with: a handpiece sized and configured to be grasped by the human hand, said handpiece having a distal end and a proximal end; an electrical signal generating apparatus which is connectable to said handpiece; an on/off switch for starting and stopping a flow of current from the electrical signal generating apparatus to the handpiece; connector apparatus to connect the distal end of the handpiece to the proximal end of said probe device and to pass said electrical current from the hand piece to the annular electrode tip of the probe.

Still further in accordance with the invention, there is provided a method for forming an opening in the lens capsule of the eye, said method generally comprising the steps of: a) providing an electrosurgical probe device comprising an elongate probe having a proximal end, a distal end, and an electrode tip formed on the distal end thereof; b) inserting the probe into the eye such that the electrode tip is in contact with the lens capsule of the eye; c) passing electrical current through the probe and to the electrode tip, said electrical current being of sufficient magnitude to form an opening in said lens capsule at the location where said electrode tip is in contact with the lens capsule.

Further objects and advantages of the present invention will become apparent to those skilled in the art upon reading and understanding of the following detailed description and the accompanying drawings.

BRIEF DESCRIPTION OF THE DRAWINGS

FIG. 3 is a rear perspective view of a monopolar embodiment of the electrosurgical probe device of the present invention.

FIG. 4 is a longitudinal sectional view of the monopolar electrosurgical probe device shown in FIG. 3.

FIG. 4A is a partial longitudinal sectional view of the distal end of the monopolar electrosurgical probe of FIG. 4.

FIG. 5 is a perspective view of a segment of hypotubing from which a notch has been removed to form an annular electrode tip usable in the electrosurgical probe devices of the present invention.

FIG. 5a is a perspective view of an annular electrode tip formed from the notched segment of hypotubing shown in FIG. 5.

FIG. 6 is a perspective cut-away view of the monopolar embodiment shown in FIGS. 3–4.

FIG. 7 is a perspective cut-away view of a first bipolar embodiment of an electrosurgical probe device of the present invention.

FIG. 8 is a cross sectional view through line 8—8 of FIG. 7.

FIG. 9 is a longitudinal sectional view of a second (alternative) bipolar embodiment of an electrosurgical probe device of the present invention.

FIG. 10 is a cross sectional view through line 10—10 of FIG. 9.

DETAILED DESCRIPTION OF THE PREFERRED EMBODIMENTS

Figure 1:
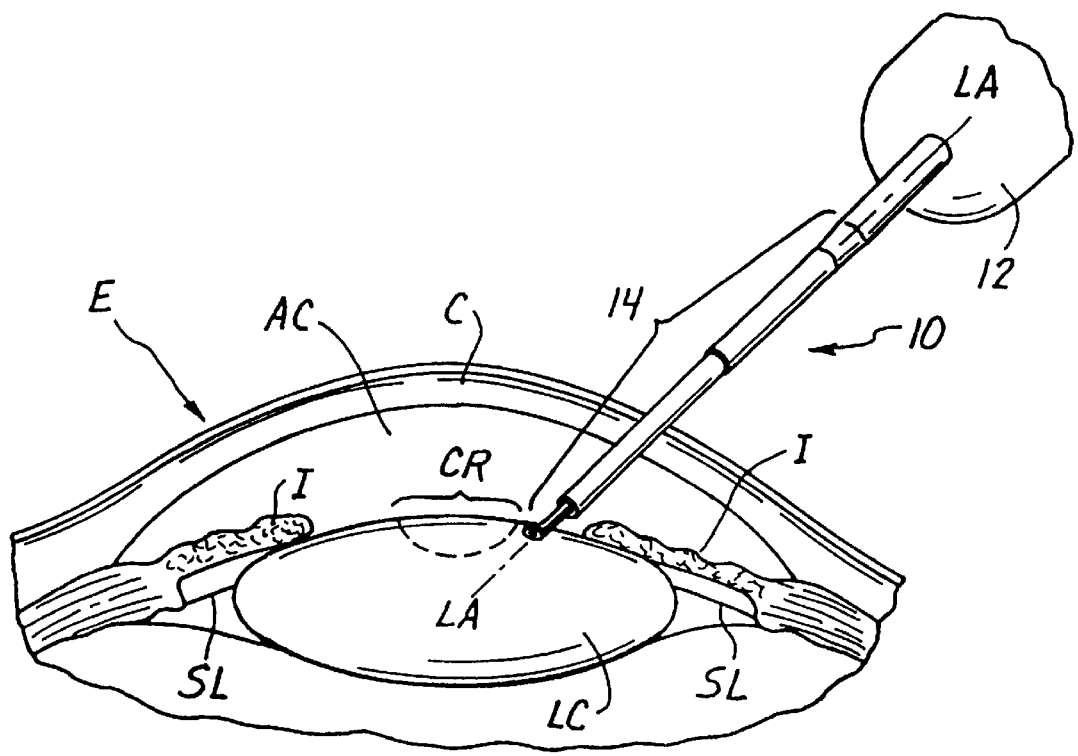
FIG. 1 is a perspective view showing an electrosurgical probe device of the present invention operatively inserted into a human eye.
Figure 1A:
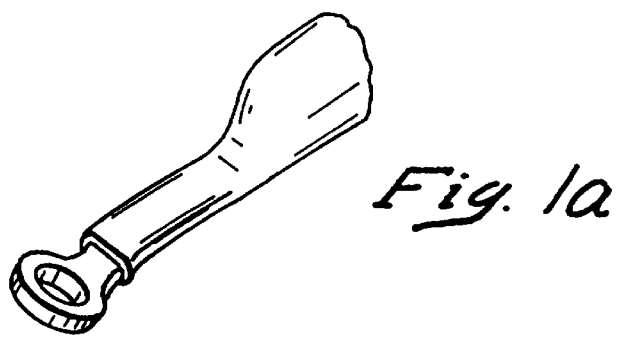
FIG. 1a is an enlarged perspective view of the distal portion of the electro-surgical probe device of FIG. 1.

The following detailed description and the accompanying drawings are provided for the purpose of illustrating and describing presently preferred embodiments of the invention only, and are not intended to limit the scope of the invention in any way.

With reference to the drawings, there is provided an electrosurgical probe device 10 which is usable to form small openings (e.g., less than 3 mm) in the anterior lens capsule LC of the eye. In general, the electrosurgical probe device 10 comprises a proximal attachment/contact hub 12 having an elongate probe member 14 extending distally therefrom, and an annular electrode tip 16 mounted on the distal end of the elongate probe portion 14. The annular electrode tip 16 is disposed at an angle relative to the longitudinal axis LA of the elongate probe portion 14.

FIG. 1 shows a preferred method by which the electrosurgical probe device 10 of the present invention may be inserted into the eye E for the purpose of forming a small (e.g., less than 3 mm) opening in the anterior lens capsule LC of the eye E. It will be noted from FIG. 1 that the lens capsule LC is suspended within the eye E, behind the anterior chamber AC and cornea C. The lens capsule LC is maintained in its normal anatomical location by various anchoring structures of the eye, including suspensory ligaments SL which are located posterior to the iris I of the eye E. A round central region CR is definable at the center if the anterior aspect of the lens capsule in direct alignment with the center of the variably-sized opening of the iris I. In operation, a small incision is formed in the cornea C and the elongate probe portion 14 of the device 10 is inserted through such incision, and is advanced through the anterior chamber AC of the eye E until the annular electrode tip 16 comes into contact with the anterior aspect of lens capsule LC, at a location outside of the central region CR, as shown. Thereafter, electrical current is passed through the annular electrode tip 16 so as to cause the tip 14 to penetrate the lens capsule LC, thereby forming an annular opening which is approximately of the same size and configuration as the annular electrode tip 16.

As the annular electrode tip 16 electrosurgically penetrates the lens capsule LC, heat will cauterize or melt the portion of the lens capsule LC which surrounds the opening formed by the electrode tip 16, thereby strengthening or reinforcing the edges of such opening. Such strengthening or reinforcement of the periphery of the opening will prevent or deter subsequent tearing, undesired enlargement or extension of the opening as the cataract removal and/or lens replacement instruments are passed through the opening.

Figure 2A:
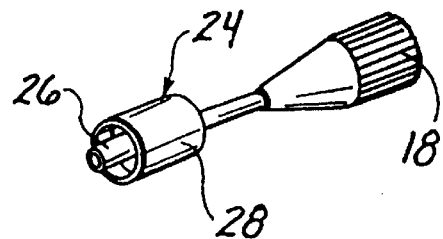
FIG. 2A is a partial perspective view of a connector assembly, formed on the distal end of the handpiece shown in FIG. 2.
Figure 2:
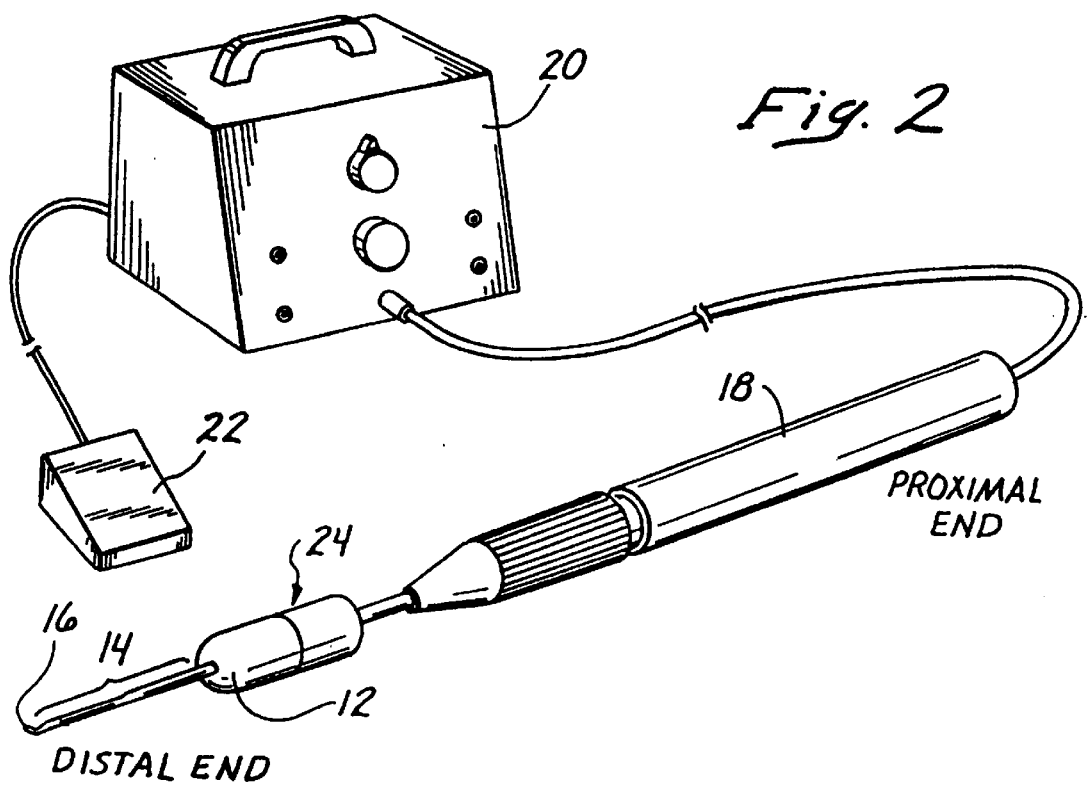
FIG. 2 is a perspective view of a system of the present invention comprising a) an electrical signal generating apparatus, b) a handpiece, and c) an electrosurgical probe device of the present invention mounted on the distal end of the handpiece.

With reference to FIG. 2–2a, the electrosurgical probe device 10 of the present invention may be constructed and configured so as to be usable as an attachment to an electrocautery system of a type typically used in ophthalmological surgery. Such electrocautery systems typically comprise a handpiece 18, an electrical signal generator 20 and an on/off switch such as a foot pedal 22.

One example of a commercially available electrocautery system of the type shown in FIGS. 2–2a is the Surgitron™ Model FFPF available from Ellman International, Inc., 1135 Railroad Avenue, Hewlett, N.Y. 11557.

In the embodiment shown in FIGS. 2–2a, a connector assembly 24 is formed on the distal end of the handpiece 18 to facilitate connection with an electrical contact to the electrosurgical probe device 10 of the present invention. In the embodiment shown, the connector assembly 24 comprises a generally cylindrical, distally extending contact post 26 surrounded by an internally threaded, rotatable, Luer-lock sleeve 24. The contact post is insertable into a receiving contact bore formed on the proximal end of the probe device 10, and the Luer-lock sleeve is then usable to engage and lock the probe device 10 to the handpiece 18 such that the contact post 26 of handpiece 18 is held in firm electrical contact with the probe device 10.

It will be appreciated that the electrosurgical probe device 10 generally described hereabove, may be specifically constructed in either monopolar or bipolar embodiments, as more fully described herebelow:

i. Monopolar Embodiments

FIGS. 3–6 show a monopolar electrosurgical probe device 10a of the present invention, which is usable in conjunction with an electrocautery system of the type shown in FIGS. 2–2a.

As shown in FIGS. 3–6, the monopolar electrosurgical probe device 10a is constructed such that the annular electrode tip 16a is the only electrode present on the body of the probe device 10a. A second electrode, such as a plate electrode (not shown), must be separately attached to or brought into proximity with the body of the patient in order that an electrical circuit or capacitive coupling be completed between the annular electrode tip 16a and such externally-placed second electrode (not shown).

As shown, the proximal hub 12a of the monopolar probe device 10a comprises an electrically conductive, generally cylindrical, hub 30 having a Leur-lock flange 32 formed therearound. An insulative covering 34, formed of polyvinyl chloride (PVC) or other suitable plastic, may be formed about the outer surface of the cylindrical hub 30, but should not interfere with the engagement of the Luer-lock flange 32 to the internal threads of the rotatable sleeve 28 of the handpiece connector assembly 24.

The distally-extending probe portion 14a of the monopolar probe device 10a may comprise a rigid base tube 36 which is continuous with and protrudes distally from the frusto-conical proximal hub 30 as shown. A first hypotube member 38 is inserted into a distal portion of the base tube 36, and extends axially therefrom, as shown. A second hypotube member 40 is inserted into a distal portion of the first hypotube member 38, and extends distally therefrom, as shown. The annular electrode tip 16a is formed on the distal end of this second hypotube member 40.

One means by which the annular electrode tip may be formed on the distal end of the second hypotube member 40 is illustrated in FIGS. 5 and 5a. With reference to FIGS. 5–5a the second hypotube member 40 has a notch 42 cut away therefrom. Such notch 42 is configured such that its distal edge is perpendicular to the longitudinal axis LA of the second hypotube member 40, and its proximal edge is curved or acutely angled relative to such longitudinal axis LA. This results in the formation of a substantially cylindrical ring at the distal end of the second hypotube member 40, such ring being connected by a remnant portion 44 of the second hypotube 40 to that proximal portion of the second hypotube 40 located proximal to the notch 42.

The distal surface DS of the cylindrical ring formed at the distal end of the second hypotube member 40 is initially disposed in a plane which is perpendicular to the longitudinal axis LA. However, the remnant portion 44 is bent in a direction away from the longitudinal axis LA such that the plane P of the distal surface of the ring member at the distal end of the second hypotube member 40 forms an internal angel A relative to the longitudinal axis LA. Also, electrically conductive wire 54 is soldered or otherwise affixed to the interior of the second hypotube member 40.

Upon assembly, the proximal portion of the second hypotube member prepared as shown in FIG. 5a, is inserted into the distal portion of the bore of the first hypotube member 38, and is affixed thereto. Similarly, the first hypotube member 38 is affixed to the base tube 36 which in turn is affixed to the frusto-conical proximal hub 30. Such direct affixation of the hypotube member 38, base tube 36 and frusto-conical proximal hub 30 may be sufficient to provide reliable electrical contact and conduction therebetween. However, if reliable electrical contact and conduction between such components is not accomplished by their direct affixation to one another, an added electrical conductive wire 54 may optionally be soldered or otherwise electrically connected to any or all of the hypotube member 38, base tube 36 and/or proximal hub 30, to facilitate electrical conduction therebetween.

The angle A of the distal surface DS of the annular electrode tip 16a of the probe device 10a may vary, depending on the intended positioning of the electrosurgical probe device 10a within the eye E. Typically, it will be desirable to position the electrosurgical probe device 10a in a manner similar to that shown in FIG. 1. Thus, in most cases, it will be desirable for the distal surface DS of the annular electrode tip 16a to form an internal angle A of no less than 90° and typically in the range of 90°–150°. In the embodiment shown, a first insulative sheath 50 is heat-shrunk or otherwise secured about the proximal portion of the second hypotube member 40 and the distal portion of the first hypotube member 38. This insulative sheath 50 helps to securely join the first 38 and second 40 hypotube members together and also provides an insulative outer covering thereon. A second insulative sheath 52 is then formed about the proximal portion of the first insulative sheath 50 and about the base tube 36.

The monopolar electrosurgical probe 10a is attachable to the connector assembly 24 of the electrocautery system shown in FIGS. 2–2a by inserting the contact post 26 of the connector assembly 24 into the proximal hub 30a such that the outer surface of the contact post 26 is in direct abutting contact with the inner surface of the frusto-conical hub 30a. Thereafter, the rotatable sleeve 24 is rotatably advanced such that the internal threads of the rotatable sleeve 34 will engage the Luer-lock flange 32a of the proximal hub 30. In this manner, electrical current from the electrical signal generator 20 will pass through the hand piece 18, from the contact post 26 and to the hub 30a of the probe device 10a. Such current will then pass from the hub 30 through the electrically conductive walls of the first 38 and second 40 hypotube members and/or through the electrically conductive wire 54. The current will then pass from the annular electrode tip 16a to a second electrode (not shown) which has been attached to or brought into proximity with the patient's body to complete the electrical circuit or establish the required capacitive coupling.

ii. Bipolar Embodiments

FIG. 7–8 show a first embodiment of a bipolar electrosurgical probe 10b of the present invention, while FIGS. 9–10 show an alternative bipolar electrosurgical probe 10c which has a structure substantially similar to (and which shares many common structural attributes with) that of the monopolar embodiment 10a described hereabove and shown in FIGS. 3–6.

With reference to FIG. 7–8, this bipolar probe device 10b of the present invention comprises an elongate probe portion 14b formed of an inner tubular electrode member 60, an outer tubular electrode member 62 and an insulating tubular sheath 64 positioned therebetween. The inner tubular electrode 60 member, outer tubular electrode member 62 and insulative tubular sheath 64 are disposed coaxially about a common longitudinal axis LA. The distal end of the inner tubular electrode 60 forms the annular electrode tip 16*b*. In the embodiment shown, this annular electrode tip 16*b* is formed by cutting the distal end of the inner tubular electrode 60 such that the it's distal surface is perpendicular (i.e., at a 90° angle) relative to the longitudinal axis LA. It will be appreciated, however, that the distal end of the inner tubular electrode 60, the outer tubular electrode 62 and/or the interposed sheath 64, may be cut at various angles relative to the longitudinal axis LA, so as to provide different angular dispositions of the annular electrode tip 16*b*. Similarly, the distal end of the outer electrode member 62 as well as the insulation sheath 64 may be axially spaced and fastened to one another such that the respective distal ends of the inner tubular electrode 60, insulation sheath 64 and outer electrode members 62 will form such angle.

The elongate probe portion 15*b* of this first bipolar probe 10*b* shown in FIG. 7–8 extends distally from and is connected to a proximal hub (not shown) which may be substantially the same as the proximal hub 12*a* described hereabove with respect to the monopolar probe device 10*a*. However, in this bipolar embodiment, only the inner tubular electrode 60 is electrically connected to the proximal hub, and the outer tubular electrode 62 is connected separately by a separate electrical connection to the signal generating apparatus 20, thereby completing the desired bipolar circuit of this embodiment.

As shown in FIG. 7, the distal end of the outer tubular electrode 62 may terminate a spaced distance proximal to the distal end of the inner tubular electrode 60. Also, the distal portion of the tubular insulating sheath 64 which protrudes beyond the distal end of the outer tubular electrode may be tapered, in the manner shown in FIG. 7. In this manner, when the bipolar probe device 10*b* is inserted into the eye, the distal end of the inner tubular electrode 60 is positioned in contact with the lens capsule LC. Thereafter, when energized, electrical current will flow between the distal end of the inner tubular electrode 60 (which forms the annular electrode tip 16*b*) the adjacent distal portion of the outer tubular electrode 62. Thus, in this first bipolar embodiment, there is no need for a separate external electrode to be attached to or brought into proximity with the patient's body, as is required of the above-described monolar polar probe device 10*a*.

FIGS. 9 and 10 shows an alternative or second embodiment of a bipolar probe device 10*c* which is similar in construction to the monopolar probe 10*a* described hereabove. This second embodiment of the bipolar probe 10*c* comprises a proximal hub 12*c* having an elongate probe portion 14*c* extending axially therefrom, in a distal direction. An annular electrode tip 16*c* is formed on the distal end of the probe portion 14*c*. The cylindrical hub 30*c*, first hypotube member 38*c*, second hypotube member 40*c*, remnant portion 44*c*, annular electrode 16*c* and electrically conductive wire 54*c* are constructed, configured and assembled in the same manner as described hereabove with respect to the monopolar embodiment.

However, in this second bipolar embodiment, an outer electrode tube 70, formed of electrically conductive material, surrounds the insulative sheet 50*c*. Such outer electrode tube 70 is connected to an electrically conductive wire 55 which extends through the insulative casing 34*c* of the proximal hub 12*c* and is connectable to the electrical signal generating device 20. The outer electrode tube 70 is distally coterminous with the insulative sheath 50*c*, such that only the remnant portion 44*c* of the second hypotube member 40*c* and the annular electrode tip 16*c* protrude distally beyond the distal end of the outer electrotube 70.

In operation, this second bipolar embodiment of the device 10*c* is inserted into the eye such that a distal portion of the probe portion 14*c* extends through the anterior chamber AC, and the distal surface DS of the annular electrode tip 16*c* is in contact with the anterior lens capsule. Thereafter, electrical current from the electrical signal generator 20 may pass through the electrically conductive wire members 54*c*, 55 and/or other electrically conductive portions of the probe device 10*c* as described hereabove, such that current will flow from the annular electrode tip 16*c* to the distal portion of the outer tubular electrode 70 through the electrically-conductive fluid environment within the anterior chamber of the eye.

It will be appreciated that the annular electrode tip 16, 16*a*, 16*b*, 16*c* described hereabove may comprise any appropriate geometrical configuration, and may have an open center (e.g., a ring or hoop) or alternatively may have a solid center (e.g., a disc having a generally annular outer edge). Furthermore, it will be appreciated that the lens capsule contacting surface, such as the distal surface, of the annular electrode tip 16, 16*a*, 16*b*, 16*c* need not be substantially flat or planar, and may be slightly concave or of any other suitable configuration. In this manner, when reference is made in this patent application to the "plane" in which the lens capsule contacting surface of the distal electrode tip lie, it will be appreciated that such plane may be projected through a concaved or wavy surface of an average variant thereof. Alternatively, in embodiments wherein the lens capsule contacting surface of the annular electrode tip 16, 16*a*, 16*b*, 16*c* is flat, such entire flat edge may lie within the referenced plane.

iii. Preferred Methods of Operating the Devices

Any and all of the above-described embodiments of the present invention are preferably operated in accordance with a general method wherein at least a distal portion of the elongate probe portion 14, 14*a*, 14*b*, 14*c* is inserted through an incision in the cornea C and is advanced through the anterior chamber AC until the lens-capsule-contacting distal surface DS of the annular electrode tip 16, 16*a*, 16*b*, 16*c* is in contact with the lens capsule LC. If a monopolar embodiment of the probe device 10*a* is used a secondary electrode will be attached to or brought into close proximity with the body of the patient at a location which is suitable to complete an electrical circuit between the annular electrode tip 16*a* of the probe 10*a* and such second electrode. On the other hand, if one of the bipolar embodiments of the probe device 10*b*, 10*c* are used, there will be no need to provide a separate second electrode with is attached to or placed in proximity with, the body of the patient.

Thereafter, the electrical signal generating device 20 is actuated so as to cause current to flow between the annular electrode tip 16, 16*a*, 16*b*, 16*c* and either the separately attached secondary electrode (monopolar embodiment) or the on-board outer electrode tube 62, 70.

Any suitable electrical wave form and power level may be used. In this regard, in at least some applications it will be desirable to use a continuous, pulsed or superpulsed wave form which provides an average power level of approximately 10 watts to form the desired opening in the anterior lens capsule.

Figure 11A:
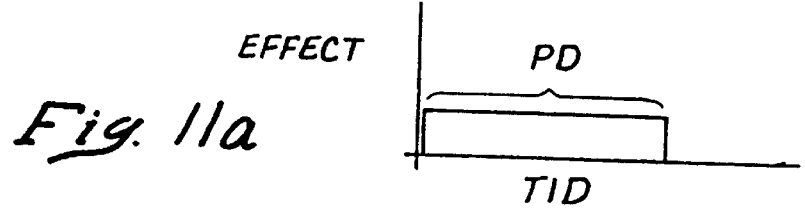
FIGS. 11a–11c are graphic representations of power vs. time, illustrating variation in the electrical wave forms and power levels which may be utilized in conjunction with the device and system of the present invention.
Figure 11B:
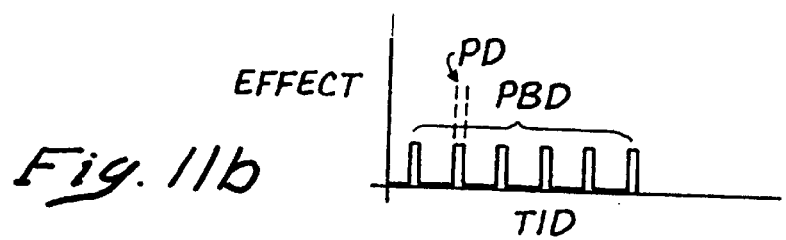
Figure 11C:
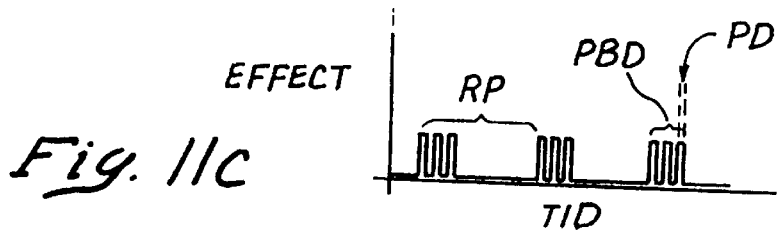

In embodiments of the system wherein the wave form is intended to be pulsed or superpulsed, the signal-generating device 20 will preferably include a mechanism for setting the desired pulse duration, pulse train duration, pulse bunch duration and/or duty cycle, examples of which are shown graphically in FIGS. 11*a*, 11*b* and 11*c*.

With reference to 11*a*, there is shown the average power generated by single pulse, of known pulse duration PD.

FIG. 11b shows the average power generated by a train of individual pulses, each of said individual pulses having a pulse duration PD, and the overall train of pulses having a pulse train duration PTD.

FIG. 11c shows a superpulsed embodiment of the invention wherein bunches of small individual pulses, each of said individual pulses having a pulse duration PD of 10 milliseconds, are generated periodically on a given repeat period RP.

It will be appreciated that the electrical signal generating device 20 may be preprogrammed to deliver desired energy levels, and/or wave form(s) in response to each triggering of a fixed on-off switch. Alternatively, the signal generating device 20 may be rheostatically controlled by way of a foot pedal or other type of rheostatic control device, and the amount and duration of energy delivered through the annular electrode tip 16, 16a, 16b, 16c will be determined by the current position of the foot pedal or other rheostatic control mechanism.

In the above-described manner, the electrosurgical probe device 10 of the present invention is usable to form an opening in the lens capsule LC of a size which is only slightly larger than the outer diameter of the annular electrode tip 16, 16a, 16b, 16c. Furthermore, when the preferred wave form and power setting are used, the resultant electrosurgical opening of the lens capsule will additionally form a heat-fused region around such opening, thereby preventing the anterior aspect of the lens capsule from being torn, enlarged or extended during the subsequent insertion and manipulation of the cataract removal device(s) and/or prosthetic lens implant introduction cannula.

The present invention has been described hereabove with reference to certain presently preferred embodiments only. No attempt has been made to exhaustively describe all possible embodiments in which the invention may be practiced. Indeed, various additions, deletions, modifications and alterations may be made to the above-described preferred embodiments without departing from the intended spirit and scope of the invention. Accordingly, it is intended that all such reasonable additions, deletions, modifications and alterations be included within the scope of the following claims.

What is claimed is:

1. A method for removing a lens from a mammalian eye through a small capsulotomy opening formed in the lens capsule of the mammalian eye leaving the central region of the anterior aspect of the lens capsule un-incised and intact, said method comprising the steps of:

A) providing a monopolar electrosurgical capsulotomy probe device which has an annular electrode tip;

B) electrically coupling a secondary electrode to the body of the patient;

C) inserting the capsulotomy device into the eye such that the electrode tip is in contact with the lens capsule at a location which is lateral to the central region of the anterior aspect of the lens capsule;

D) passing electrical current through the probe and to the electrode tip, said electrical current being of sufficient magnitude to form a capsulotomy opening at said location while allowing the central region of the anterior aspect of the lens capsule to remain in tact;

E) removing the capsulotomy device from the eye;

F) providing a lens reduction device which comprises an elongate probe having a rotating lens reducing head;

G) inserting the lens reduction device through the capsulotomy opening created in Step D such that the rotating lens reducing head becomes positioned within the lens capsule;

H) causing the lens reducing head to rotate so as to effect endocapsular reduction of the lens; and, (I) removing the reduced matter of the lens from the lens capsule through the capsulotomy opening created in Step D.

2. The method of claim 1 wherein the electrical coupling said secondary electrode to the body of the patient comprises attaching said secondary electrode to the body of the patient, in abutting contact therewith.

3. The method of claim 1 wherein the electrical coupling said secondary electrode to the body of the patient comprises positioning said secondary electrode in close but not abutting proximity to the body of the patient to establish capacitive coupling between the body of the patient and said secondary electrode.

4. The method of claim 1 wherein Step D further comprises:

passing an electrical current having a power of approximately 10 watts, through the probe and to the electrode tip.

5. The method of claim 1 wherein the electrical current which is passed through the probe in Step D of the method comprises pulsed electrical current.

6. The method of claim 1 wherein the electrical current passed through the probe in Step D the method comprises bunches of pulses of electrical current separated by intervening period of at least minimal electrical current.

7. The method of claim 1 wherein the electrical current passed through the probe in Step D the method is super pulsed electrical current.

8. The method of claim 1 wherein Step D further comprises:

passing electrical current of a generally sinusoidal weave from through the probe and to the electrode tip.

9. The method of claim 1 wherein the capsulotomy opening created in Step D is less than 3 millimeters in cross-dimension.

* * * * *